(12) United States Patent
Knowles et al.

(10) Patent No.: US 8,999,419 B2
(45) Date of Patent: Apr. 7, 2015

(54) ENHANCEMENT OF POTATO TUBER SPROUTING INHIBITORS USING VARIOUS COMBINATIONS OF AGENTS

(75) Inventors: Lisa Knowles, Pullman, WA (US); Norman R. Knowles, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 13/820,183

(22) PCT Filed: Sep. 2, 2011

(86) PCT No.: PCT/US2011/050286
§ 371 (c)(1),
(2), (4) Date: Mar. 19, 2013

(87) PCT Pub. No.: WO2012/031174
PCT Pub. Date: Mar. 8, 2012

(65) Prior Publication Data
US 2013/0183419 A1    Jul. 18, 2013

Related U.S. Application Data

(60) Provisional application No. 61/379,473, filed on Sep. 2, 2010.

(51) Int. Cl.
*A23B 7/154*   (2006.01)
*A23L 1/216*   (2006.01)
*A23L 3/34*    (2006.01)
*A01N 35/02*   (2006.01)

(52) U.S. Cl.
CPC ............... *A23B 7/154* (2013.01); *A01N 35/02* (2013.01)

(58) Field of Classification Search
USPC ............ 426/89, 102, 321, 615, 637, 654
See application file for complete search history.

(56) References Cited

U.S. PATENT DOCUMENTS

| | | | | |
|---|---|---|---|---|
| 5,129,951 | A * | 7/1992 | Vaughn et al. | 504/348 |
| 5,139,562 | A * | 8/1992 | Vaughn et al. | 504/292 |
| 5,436,226 | A * | 7/1995 | Lulai et al. | 504/291 |
| 5,580,596 | A * | 12/1996 | Winkelmann et al. | 426/321 |
| 5,622,912 | A * | 4/1997 | Riggle et al. | 504/143 |
| 5,635,452 | A * | 6/1997 | Lulai et al. | 504/324 |
| 6,855,669 | B2 * | 2/2005 | Knowles et al. | 504/348 |
| 2007/0135307 | A1 | 6/2007 | Olson et al. | |
| 2007/0290062 | A1 | 12/2007 | Forsythe et al. | |
| 2009/0062126 | A1 | 3/2009 | Knowles et al. | |

* cited by examiner

*Primary Examiner* — Leslie Wong
(74) *Attorney, Agent, or Firm* — Whitham Curtis Christofferson & Cook, PC

(57) ABSTRACT

Compositions and methods for inhibiting the sprouting of potato tubers are provided. The compositions comprise combinations of i) α,β-unsaturated aliphatic aldehydes, and ketones, C3 to C14 aliphatic aldehydes and ketones, and/or C3 to C7 saturated or unsaturated primary and secondary aliphatic alcohols; and 2) conventional sprout Inhibitors, The effect of the combinations is additive and/or synergistic, and less of the conventional inhibitor is required to achieve the same or improved levels of sprout inhibition.

24 Claims, 2 Drawing Sheets

ENHANCEMENT OF POTATO TUBER SPROUTING INHIBITORS USING VARIOUS COMBINATIONS OF AGENTS

BACKGROUND OF THE INVENTION

1. Field of the Invention

The invention generally relates to using α,β-unsaturated aliphatic aldehydes and ketones, C3 to C14 aliphatic aldehydes and ketones, and C3 to C7 aliphatic primary and secondary saturated and unsaturated alcohols in combination with conventional sprout inhibitors to inhibit sprouting of potato tubers, thereby reducing the amount of conventional inhibitor that is applied.

2. Background of the Invention

Following harvest, potato tubers undergo a natural period of dormancy during which sprout growth is inhibited by endogenous hormones. As tubers emerge from dormancy and begin to sprout, respiration increases, starch is catabolized to sugars, and weight loss increases. The result is a decrease in quality of tubers destined for fresh and processing markets. Hence, inhibition of sprouting through chemical or physical means preserves quality and prolongs the duration of storage.

The sprout inhibitors registered for use on potatoes in the United States include CIPC (also known as chlorpropham, Sprout Nip®, etc.), maleic hydrazide (MH), DMN (also known as dimethylnaphthalene, 1,4SIGHT®, 1,4SEED®, 1,4SHIP®), DIPN (diisopropylnaphthalene, Amplify®), and clove oil (Biox-C®; Sprout Torch™). Except for MH, which is applied pre-harvest to actively growing plants, all inhibitors are applied post harvest when tubers are in the storage bin.

CIPC is the most effective and most widely used potato sprout inhibitor. This chemical agent is most often applied as a thermal aerosol fog into potato storages after wound-healing and prior to sprouting. In the Pacific Northwest, this is usually in November or December, before dormancy has ended. The chemical is fogged into storage at the recommended rate of 1 lb chlorpropham/600 cwt. One gallon of CIPC aerosol grade will treat 4200 cwt (210 tons) of potatoes. CIPC can inhibit sprouting and extend the storage life of table-stock and processing potatoes for up to 1 year with two applications.

CIPC is an effective sprout suppressant that has been used in the potato industry for about 40 years and the EPA considers it as a group E chemical (non-carcinogenic). CIPC was originally registered in the United States as a pre- and post-emergence herbicide in 1962 and the EPA has set residue limits for potato tubers. Notwithstanding its safety record, the trend today is to reduce the use of synthetic pesticides in agriculture in order to reduce residues in the world's food supply. The chemical is continually being scrutinized by the EPA as it is among the three pesticides found in the highest concentrations in the average American diet and constitutes over 90% of the total synthetic residues found in U.S. potatoes (Gartrell et al., 1986). In July 2008, the Environmental Protection Agency (EPA) lowered the residue level on potatoes from 50 ppm to 30 ppm. Among many European countries, the residue level of potatoes is set at 10 ppm. The economic importance of this chemical as a sprout inhibitor to the potato industry is illustrated by the fact that it accounts for a majority of the sprout suppressant treatments in many countries and the registrants allocated considerable resources in the re-registration of CIPC. While other potential sprout suppressant agents have been identified (e.g. aromatic aldehydes and alcohols, methyl esters of rape oil, carvone, jasmonates, spearmint and peppermint oils), none appear as effective as CIPC. There remains an ongoing need to provide alternative sprout inhibitors that are safe and effective, particularly sprout inhibitors that are natural compounds, and that do not pose a threat to the environment or to the health of humans and other species.

1,4SIGHT® (94.7% DMN=1,4-dimethylnaphthalene) is one such natural chemical agent that is also registered for sprout control, but it tends to be less effective than CIPC. DMN is naturally produced in potatoes. It is more volatile than CIPC and thus dissipates from tubers more rapidly than CIPC. Multiple applications of DMN are required to maintain season-long sprout inhibition. DMN is vaporized and applied as an aerosol into bulk storages. It can be applied any time after tubers are placed in the bin but is usually applied later in the fall or early winter when sprouting potential begins to increase. DMN is registered for use at a rate of 1 lb DMN/500 cwt (=20 ppm on a DMN to potato weight basis). Because of the need for multiple applications of DMN to achieve prolonged inhibition of sprouting, DMN is more costly to use than CIPC.

Other natural volatile sprout inhibitors have been identified. Carvone (derived from caraway seed) is commercially available for use on potatoes in the Netherlands (Hartmans et al 1995. The following US patents describe the use of various compounds for the inhibition of potato sprout formation: U.S. Pat. No. 5,436,226 to Lulai, et al. (Jul. 25, 1995) describes the use of jasmonates; U.S. Pat. No. 5,635,452 to Lulai et al (1997) describes the use of aromatic acids, U.S. Pat. No. 6,855,669 to Knowles and Knowles (2005) describes the use of α,β unsaturated aldehydes and ketones, U.S. Pat. No. 5,580,596 to Winkelmann et al. (Dec. 3, 1996) describes the use of rape seed oil and certain long-chain alcohols, either alone or in combination; U.S. Pat. No. 5,139,562 to Vaughn et al., (Aug. 16, 1992) describes the use of volatile monoterpenes (e.g. from eucalyptus, peppermint, spearmint, etc.); and U.S. Pat. No. 5,129,951 to Vaughn et al., (Jul. 14, 1992) describes the use of aromatic aldehydes and alcohols. In addition, Vokou et al. (1993) have demonstrated that the essential oils from a multitude of herbs (e.g. sage and rosemary) possess sprout inhibiting activity in potatoes.

Despite the promise of these diverse compounds, CIPC remains by far the most effective sprout inhibitor but the presence of chemical residues on potatoes is of concern globally. Therefore, as an alternative to the complete replacement of CIPC, a reduction in application rate of CIPC would be beneficial though this may lead to poor or erratic sprout control. In U.S. Pat. No. 5,622,912 a method for decreasing CIPC residue via combination with DIPN or DMN is described. Supporting data demonstrated that an application rate of 14 ppm CIPC in combination with 56 ppm DMN or DIPN resulted in a greater percentage of marketable tubers compared to 14 or 22 ppm CIPC alone following a storage period.

SUMMARY OF THE INVENTION

The invention provides compositions and methods which permit the use of lower amounts of conventional sprout inhibitors while maintaining the same, or improved, levels of sprout inhibition. The methods involve the use of combinations of inhibitors, at least one member of the combination being: a C3 to C14 α,β-unsaturated aliphatic aldehyde or ketone, a C3 to C14 saturated aliphatic aldehyde or ketone; or a C3 to C7 saturated or unsaturated aliphatic primary or secondary alcohol; and the other member of the combination being a conventional sprout inhibitor.

According to the present invention α,β-unsaturated and saturated carbonyl compounds as well as saturated and unsaturated primary and secondary alcohols are used in combination with reduced application rates of a conventional inhibitor such as CIPC to achieve long-term potato sprout control. Preliminary studies have shown that unexpectedly, the use of trans-2-nonenal followed by CIPC provided sprout control for a longer period compared to either compound used alone. Thus, the present invention provides methods for inhibiting potato tuber sprouts, the methods utilizing a lower dosage conventional inhibitor (e.g. CIPC) if one or more of the presently disclosed sprout inhibitor compounds is used in various types of mixtures or sequential applications with the conventional inhibitor.

DETAILED DESCRIPTION OF THE PREFERRED EMBODIMENTS OF THE INVENTION

Figure 1:
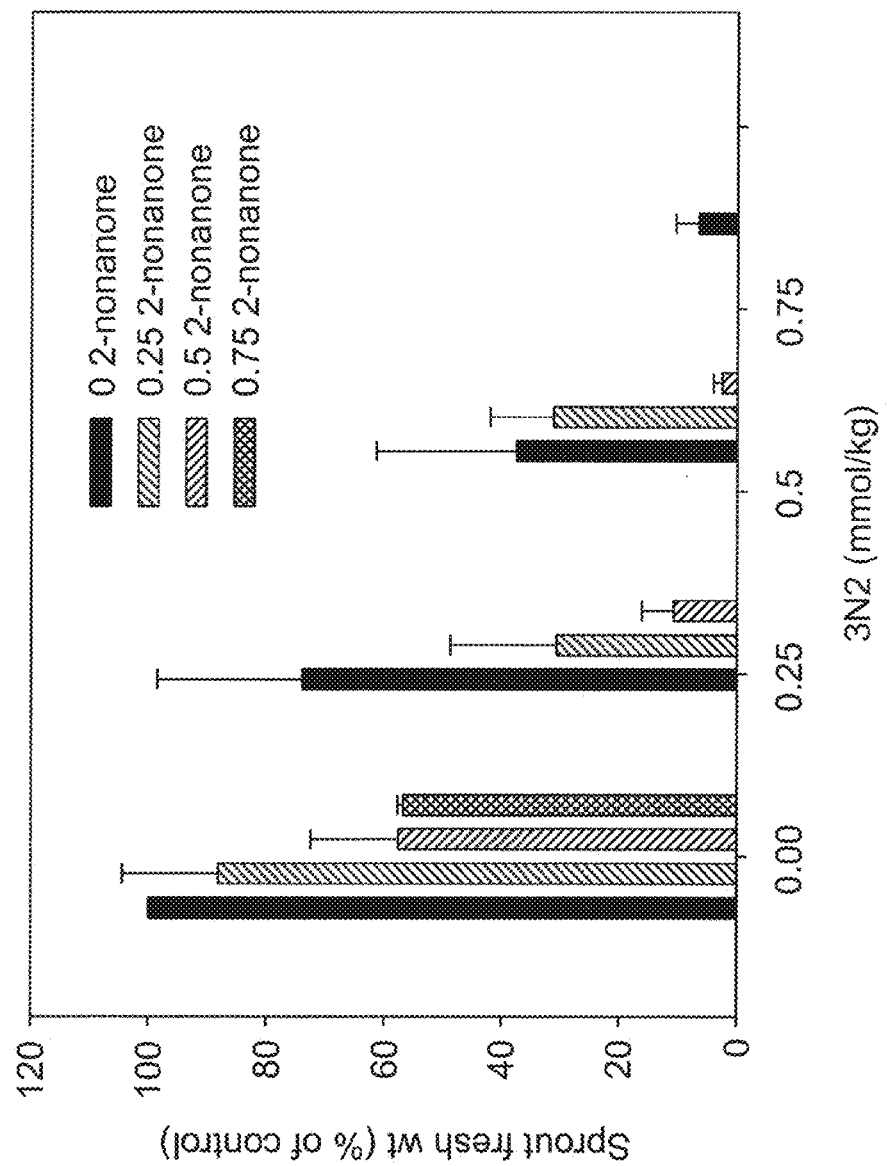
FIG. 1. Effects of 3-nonen-2-one (3N2) in various combinations with 2-nonanone on sprouting of Russet Burbank tubers. The compounds were applied as described in Example 1. Tubers were treated for 24 h, removed from treatment chambers, and placed at 22° C. to sprout for 3 weeks. Sprout fresh weight is expressed as a percentage of control (non-treated), which were 100% sprouted.

The present invention provides combinations of two categories of agents to inhibit (e.g. prevent, forestall, slow, reverse, or otherwise hinder) sprouting of potato tubers. The first category of agents includes one or more of 1) a C3 to C14 aliphatic aldehyde or ketone; and/or 2) a C3 to C7 aliphatic saturated or unsaturated primary and secondary alcohol; and/or 3) a C3 to C14 α,β-unsaturated aldehyde or ketone. The second category of agent includes known, conventional sprout inhibitors. Use of these two categories in combination allows the use of lower amounts of the conventional inhibitor while achieving substantially the same or improved levels of sprout inhibition.

Suitable C3 to C14 α,β-unsaturated aldehydes and ketones are described in U.S. Past. No. 6,855,669, the complete contents of which are hereby incorporated by reference. Suitable C3 to C14 aliphatic aldehydes and ketones and C3 to C7 aliphatic saturated or unsaturated primary and secondary alcohols (which are metabolites of C3 to C14 α,β-unsaturated aldehydes and ketones) are described in co-pending U.S. patent application Ser. No. 12/186,861 (published as US 2009-0062126 the complete contents of which are hereby incorporated by reference) and are described in detail below. The metabolites may be applied directly to potato tubers as "first components", or indirectly as a result of the application of C3 to C14 α,β-unsaturated aldehydes and ketones parent compounds, the metabolites appearing on the tubers as breakdown products.

The first category of agents may be referred to herein e.g. as "the compounds described herein", the "sprout inhibitors described herein", or as the "first" agent, inhibitor, compound, etc. The second category of agents may be referred to e.g. as "known" or "conventional" or "additional" inhibitors, or as the "second" agent, inhibitor, compound, etc. The chemical structure and characteristics of the first inhibitor differ from those of the second, conventional inhibitor.

Conventional inhibitors that may be used in the practice of the invention include but are not limited to: chlorpropham (CIPC), dimethylnaphthalene (DMN), diisopropylnaphthalene (DIPN), carvone, clove oil, mint oil or other essential oils, ethylene gas, etc. Examples of some combinations of agents of the invention with conventional agents include but are not limited to: trans-2-nonenal plus CIPC; 2-nonanone plus MH, 3-decen-2-one plus CIPC, 3-decen-2-one plus DMN, 2-decanone plus DIPN, 3-decen-2-one plus clove oil, 3-nonen-2-one plus CIPC, etc.

Methods of applying the two categories of inhibitors are also provided. Such methods are generally carried out after the tubers are harvested, i.e. during storage, although this need not always be the case. In some embodiments, maleic hydrazide (MH), is also utilized although not as a component of a mixture per se. Rather, MH may be applied pre-harvest and prior to the post-harvest application of one or more of the compounds described herein, or prior to the application of a mixture of the two categories of inhibitors as described herein. In other words, MH may be used in methods involving the sequential application of inhibitors but not in e.g. single tank mixtures.

The treatment of tubers with a combination of inhibitors may be carried out by any suitable method known to those of skill in the art. For example, at least one sprout inhibitor as described herein and at least one conventional inhibitor may be mixed together into a single composition for delivery to the tubers. The two are then applied simultaneously, e.g. as a single tank mixture. In this embodiment, the sprout inhibitors described herein are combined, e.g. with one or more of CIPC, DMN, DIPN, carvone, mint, clove, various essential oils (but not maleic hydrazide) in a ratio ranging from about 1 to about 99% well before application.

Formulations of the sprout inhibitors of the invention include but are not limited to: 1) "application mixtures" that are prepared by combining two or more inhibitors (e.g. two or more commercial products) before application; this embodiment may be a temporary, short-lived mixture that is made up "on the spot" at the time of application, i.e. just before or shortly before use; and 2) "pre-application mixtures" which are commercial products that are specifically formulated to contain two (or more) inhibitors (e.g. CIPC+3D2), and which can be purchased off-the-shelf as one product.

Alternatively, separate preparations of the two categories of inhibitors are used and each type of inhibitor is applied to the tubers separately (solo application). Exposure of the tubers to the separate inhibitor preparations may occur simultaneously or substantially simultaneously, e.g. by simultaneous fogging from two or more sources (e.g. cold or thermal-electric, internal combustion or gas fired); by direct spraying; or by misting or humidification systems or other commercially available applications systems; or via tank mixed, co-injections from multiple or separate injection systems into the same applicator or application system, etc. In some embodiments, application is not strictly simultaneous, but is substantially so e.g. one inhibitor is applied and then the second inhibitor is applied immediately thereafter, or as soon as is practically possible or convenient. In this embodiment, the time interval between applications is minimal, e.g. on the order of minutes or hours, or at most a few days. Thus, exposure of the tubers to the two categories of inhibitors overlaps for at least a portion of the exposure period, and usually for most of the exposure period.

Alternatively, the application of the two different inhibitors may be carried out sequentially, i.e., one inhibitor is applied, an interval of time is allowed to lapse, and then the second inhibitor is applied. Typically, the timing of the separate applications is spaced apart by a week to several weeks, or even months (e.g. 1-3 months). In some embodiments, applications are planned so that the second application occurs approximately when the effects of the first application are waning, i.e. when sprouts begin to appear on the tubers. Alternatively, when the probable duration of the effect of an inhibitor is already known, application of the second inhibitor may be scheduled for a time before sprouting actually begins, e.g. for a time which is a few days or weeks prior to a date when sprouts are likely to appear, based on past experience. In some embodiments of sequential applications, a conventional inhibitor is applied first and an inhibitor as described herein is applied later. Advantages of this strategy include that, by the end of storage, very little if any conventional inhibitor residue is still present. First category agents include several natural products and are relatively non-toxic. Thus, even if residual first agent inhibitor remains, handling and consumption of the tubers is safe. However, the order of application may be reversed, i.e. inhibitors described herein are applied first and the application of a conventional inhibitor follows. In either case, the use of two different categories of inhibitors advantageously permits the use of lower quantities of conventional inhibitor.

Generally, a total of two applications of inhibitor are carried out. An exemplary embodiment would be utilizing a thermal fogging system to apply a conventional inhibitor such as CIPC at a low rate (e.g. 5-8 ppm) within a few weeks (e.g. 2-8 weeks) after potatoes have been transferred post-harvest into storage. After a time interval of from about 30-45 days, the agents described herein are applied also using a thermal fogging system. However, repetitive applications of one or both of the two categories of sprout inhibitor are also encompassed, e.g. conventional inhibitor may be applied, followed by application of at least one inhibitor of the present invention, followed by one or more additional applications of at least one inhibitor of the present invention, etc.

In all embodiments of the invention, the first component of the combination and the second component of the combination includes at least one, and may include more than one, agent. In other words, a mixture of "first" agents may be applied as the first component of the combination and a mixture of "second" agents may be applied as the second component. If a plurality of either category of inhibitor is used, the plurality may be applied as a single preparation or individually from separate preparations.

According to the invention, when combinations of agents are used as described herein, the amount of conventional inhibitor that is employed to obtain the same or substantially the same level of sprout inhibition (or even greater levels of sprout inhibition) is lower than would otherwise be required. For example, the amount of CIPC that is normally applied when used alone is in the range of from about 16 to about 20-22 mg of CIPC per kg of potato tubers. However, by using the methods of the invention and combining the use of CIPC with the use of one or more sprout inhibitors as described herein, (e.g. when a combination of CIPC and T2N is used), the amount of CIPC can be reduced (decreased) to an amount or level in the range of from about 1 to about 14 mg/kg; while achieving essentially the same level (or an even higher level) of sprout inhibition. The amount of e.g. trans-2-nonenal or 3-decen-2-one or other sprout inhibitor described herein that is used in such combinations is generally in the range of from about 0.1 to about 3 mmol/kg of tubers.

In all embodiments described herein, additional surfactants or adjuvants which enhance or aid in application and deposition of the agents on the surface of potato tubers may also be employed.

In some embodiments of the invention, the effect of combining inhibitors is additive. Alternatively, the effect of using a combination of inhibitors may be synergistic in a classical sense and the effect is non-additive, i.e. the result of using a combination of inhibitors causes a decrease in sprout development (or expressed conversely, an increase in the inhibition of sprout formation) that is greater than the sum of the decreases that are observed when the inhibitors are used separately. Generally, the increase in sprout inhibition is in the range of from at least about 5 to 100% (or even more) greater than would be predicted or expected, based on the known level of sprout inhibition that is observed when the inhibitory agents are used separately. In some embodiments, two agents are used, but the invention also encompasses the use of three or more (e.g. 4, 5, 6, 7, 8, 9, 10 or more) inhibitors together.

In some embodiments, the first sprout inhibiting agent is an α,β-unsaturated aliphatic aldehyde or an α,β-unsaturated aliphatic ketone and metabolic breakdown products which inhibit potato tuber sprouting are formed therefrom. The metabolic breakdown products include C3 to C14 saturated aliphatic aldehydes, C3 to C14 saturated aliphatic ketones, C3 to C7 saturated or unsaturated aliphatic primary alcohols; and C3 to C7 saturated or unsaturated aliphatic secondary alcohols. In other embodiments, the breakdown products themselves are used as the first agent.

Aliphatic C3 to C14 aldehydes that may be used in the practice of the invention generally have the chemical formula

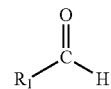

where $R_1$ is a C2 to C13 branched or unbranched, substituted or unsubstituted saturated alkyl or a C2 to C13 branched or unbranched, substituted or unsubstituted unsaturated alkenyl. In some embodiments of the invention, the aldehyde is nonanal,

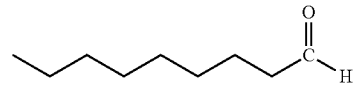

or decanal,

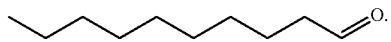

Aliphatic C3 to C14 ketones that may be used in the practice of the invention generally have the chemical formula

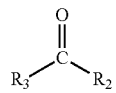

where $R_2$ and $R_3$ are C1 to C12 branched or unbranched, substituted or unsubstituted saturated alkyl or a C1 to C12 branched or unbranched, substituted or unsubstituted unsaturated alkenyl. $R_2$ and $R_3$ may be the same or different. The sum of the carbons in $R_2+R_3$ does not exceed 13. In some embodiments of the invention, the ketone is 2-nonanone, or 2-decanone, Aliphatic C3 to C7 primary alcohols that may be used in the practice of the invention generally have the chemical formula where $R_4$ is a C2 to C6 branched or unbranched, substituted or unsubstituted saturated alkyl or a C2 to C6 branched or unbranched, substituted or unsubstituted unsaturated alkenyl. In various embodiments of the invention, the unsaturated C3 to C7 primary alcohol is 1-hexanol    1-heptanol trans-2-hexen-1-ol trans-2-hepten-1-ol The aliphatic C3 to C7 secondary alcohols that may be used in the practice of the present invention generally have the chemical formula where $R_5$ and $R_6$ is a C1 to C5 branched or unbranched, substituted or unsubstituted i saturated alkyl or a C1 to C5 branched or unbranched, substituted or unsubstituted unsaturated alkenyl. The sum of the carbons in $R_5+R_6$ does not exceed 6, $R_5$ and $R_6$ may be the same or different. In one embodiment of the invention, the saturated C3 to C7 secondary alcohol is 2-heptanol, In addition, various C8 to C14 primary and secondary alcohols may be used in the practice of the invention. These compounds may be provided directly or may be provided via the breakdown of α,β-unsaturated aliphatic aldehydes and/or α,β-unsaturated aliphatic ketones as described herein. C8 to C14 primary alcohols have the general formula Where R7 is a C7 to C13 branched or unbranched, substituted or unsubstituted saturated alkyl or a C7 to C13 branched or unbranched, substituted or unsubstituted unsaturated alkenyl.

C8 to C14 secondary alcohols have the general formula where R8 is a C1 to C12 branched or unbranched, substituted or unsubstituted saturated alkyl or a C1 to C12 branched or unbranched, substituted or unsubstituted unsaturated alkenyl; and R9 is a C1 to C12 branched or unbranched, substituted or unsubstituted saturated alkyl or a C1 to C12 branched or unbranched, substituted or unsubstituted unsaturated alkenyl. The sum of R8 and R9 is not less than 7 and does not exceed 13.

Examples of additional compounds that may be used in the practice of the invention include but are not limited to the following:

Aliphatic C3 to C14 aldehydes that may be used in the practice of the present invention include but are not limited to: propanal, butanal, pentanal, hexanal, heptanal, octanal, 4-nonenal, 6-nonenal, decanal, undecanal, dodecanal, tridecanal, and tetradecanal.

Aliphatic C3 to C14 ketones that may be used in the practice of the present invention include but are not limited to: propanone, 2-butanone, 2-pentanone, 2-hexanone, 2-heptanone, 2-octanone, 3-octanone, 3-nonanone, 2-decanone, 3-decanone, 2-undecanone, 2-dodecanone, 2-tridecanone, and 2-tetradecanone.

Aliphatic C3 to C7 primary alcohols that may be used in the practice of the invention include but are not limited to: 1-propanol, 1-butanol, 2-buten-1-ol, 1-pentanol, 2-penten-1-ol, 1-hexanol, 2-hexen-1-ol, and 1-heptanol.

Aliphatic C3 to C7 secondary alcohols that may be used in the practice of the present invention include but are not limited to: 2-propanol, 2-butanol, 2-pentanol, and 2-hexanol.

Aliphatic C8 to 14 primary alcohols that may be used in the practice of the invention include but are not limited to: 1-octanol, 1-decanol and 2-nonen-1-ol.

Aliphatic C8 to C14 secondary alcohols that may be used in the practice of the present invention include but are not limited to: 2-octanol, 2-nonanol, and 2-decanol By "substituted" we mean the replacement of hydrogen with a monovalent or divalent radical. Suitable substitution groups include but are not limited to, for example, hydroxyl, nitro, amino, imino, cyano, halo, thio, thioamido, amidino, imidino, oxo, oxamidino, methoxamidino, guanidino, sulfonamido, carboxyl, formyl, lower alkyl, halo-lower alkyl, lower alkoxy, halo-lower alkoxy, lower alkoxyalkyl, alkylcarbonyl, cycloalkyl, heterocycloalkyl, alkylthio, aminoalkyl, cyanoalkyl, and the like.

The application of sprout inhibiting compounds to potato tubers is generally known to those of skill in the art. The treatment of potato tubers is described, for example, in U.S. Pat. No. 6,855,669 (Knowles et al.), the complete contents of which are hereby incorporated by reference. Application is typically to bulk potatoes in storage bins, although this need not be the case as the compounds may be applied to potatoes stored or sorted in any manner, so long as sufficient contact is made between the compounds and the potato tubers to inhibit sprouting. Application of the compounds to the potatoes may be carried out by any of several methods. Generally, the compound(s) will be volatilized, e.g. by cold fogging, or at high temperature (which utilize various heat sources such as gasoline, propane, butane, natural gas, electric, etc.) to create a thermal fog, or by atomization, and introduced into storage bins e.g. via the ventilation system. This introduction may be a discrete event that is carried out once or multiple times throughout the storage period. Alternatively, a slow-release mechanism or formulation may be employed in which the compound gradually enters the storage area over a longer period of time, for example by evaporation from a source impregnated with the compound(s). Further, the compounds may also be advantageously applied by spraying or misting a liquid form of the compound onto the potatoes, or by dipping or otherwise coating the potatoes with the compound, either prior to, during, or after the potatoes are stored (e.g. between storage and boxing or bagging for commercial purposes). Such compounds can also be used to coat or impregnate consumer containers (such as cardboard boxes, burlap bags, plastic bags etc) which typically hold potatoes coming out of storage sheds or bins for the express purpose of making available the precursor or metabolite compounds to delay sprouting in transit and at final destinations (e.g. homes, grocery stores, restaurants and other food establishments). For such applications, the compounds may also be mixed with various other agents known to facilitate the delivery of gases, liquids, or gels as appropriate (e.g. emulsifiers, slow release agents or matrices and the like). Other means of delivering the sprout inhibitors include but are not limited to employing tank mixtures of the combination of inhibitors. Any delivery method known in the art may be used.

The timing of exposure of the potatoes to the compounds of the invention can be prior to or after emergence from dormancy.

The application of the compounds (including mixtures) may be carried out only once as described above (i.e. early in the storage of the potatoes and even prior to sprouting). Alternatively, depending on the factors such as the cultivar, the time of harvest of the potatoes, the length of storage of the potatoes, the intended use of the potatoes, etc. multiple applications of the compounds may be made. For example, if the potatoes are to be used as seed potatoes, only one application may be necessary as the eventual sprouting of the potatoes will be desirable. However, if the potatoes are to be stored long term (e.g. over the entire winter for distribution in the spring or the following summer) multiple applications may be made. In this case, the first application will generally be made early in the storage process (e.g. at between 4 and 32 weeks following harvest), and subsequent applications may also be made at roughly 4 to 12 week intervals as needed, until the potatoes are retrieved for use.

The amount of compound (or compounds) which is applied is sufficient to terminate, slow, prevent, and/or inhibit sprout growth on the potato tubers. The development of sprouts may thus be prevented altogether, or the onset of sprouting may be delayed, or existing sprouts may be killed, or the development of sprouts may be slowed compared to untreated tubers, etc. In any case, the process of sprouting is, in general, inhibited by treating the potato tubers with the compounds as described herein, or with their precursor compounds (e.g. see U.S. Pat. No. 6,855,669, for examples of precursor α,β-unsaturated aldehydes and ketones which can be used to make the ketones and aldehydes and alcohols of this invention), in comparison to potato tubers that are not exposed to or contacted by the compounds in a similar manner. In general, such inhibition will result in a decrease in the number, length, or fresh weight of sprouts developing on the tubers, and/or a decrease in the rate of growth (as determined by length, number, and/or weight) of sprouts that develop on the treated tubers, in comparison to potato tubers that are not exposed to or contacted by the compounds. The decrease will be in the range of at least about 10 to 100%, preferably in the range of about 50 to 100%, and most preferably in the range of about 75 to 100%. Thus, the treated tubers will display a decrease in sprout development of about 10, 20, 30, 40, 50, 60, 70, 80 90, or 100%, compared to untreated tubers. The sprout free-period following treatment will be between 21 and 100 days and in some cases as much as six months.

According to the present invention, the compounds of the invention may be applied directly, or they may arise indirectly as metabolites from the application of precursor compounds such as, but not limited to, those described herein and in U.S. Pat. No. 6,855,669. The compounds of the invention may also be derived from the application of a formulation of an inactive chemically related species which is released as an active form upon application to tubers. Examples of this chemistry are an acetal or hemiacetal of the active aldehyde or the ketal or hemiketal of the active ketone. The compounds are applied in combination with other agents used to treat potatoes, examples of which include but are not limited to other substances that also inhibit sprouting. In this case, the use of the compounds of the present invention may allow the use of less of another substance (either by lower dosage or fewer applications) whose use is less desirable (e.g. a substance that is not naturally occurring, is more expensive, toxic, etc). Such combinations may also allow the use of lower doses of the compounds of the present invention.

The preparation of the compounds for use in the practice of the present invention is known to those of skill in the art. Many of the compounds are commercially available. Others may be synthesized by well-known methods. Still others may be isolated from natural sources, e.g. from potatoes or other plants in which they are naturally produced, or in which their precursors are produced. Alternatively, the compounds may be produced in plants or other organisms that have been genetically engineered to overproduce the compounds. One advantage of the method of the present invention is that some of the compounds that are used in the method may be relatively inexpensive to procure, or can be expected to arise from the metabolism of relatively inexpensive α,β-unsaturated carbonyls that have been applied to potato tubers, and thus may offer an advantage when compared to more costly alternatives.

The following non-limiting examples serve to further illustrate the practice of the invention.

EXAMPLES

Example 1

Use of Mixtures of 3-nonen-2-one (3N2) and 2-nonanone as Inhibitors of Sprouting of Potato Tubers The objective of this study was to determine the efficacy of mixtures of 3N2 and its metabolite, 2-nonanone, on sprout inhibition. Potato tubers were treated for 24 h in a closed chamber. The chemicals were volatilized from filter paper inside the chamber. Treatment was with 0 to 0.75 mmol/kg of 3N2 combined factorially with 0 to 0.75 mmol/kg of 2-nonanone. The treated tubers were placed at 22° C. and sprout fresh weights were measured 21 days after treatment. Sprout growth from tubers treated with 0.5 and 0.75 mmol/kg 2-nonanone averaged 58% of non-treated tubers, compared with 9% for 0.75% 3N2 applied alone (FIG. 1). The 0.25 mmol/kg 3N2+0.5 mmol/kg 2-nonanone treatment inhibited sprouting to the same extent as the 0.75 mmol/kg 3N2 treatment.

Example 2

Use of Combinations of Trans-2-nonenal and a Conventional Inhibitor, CIPC

Figure 2A:
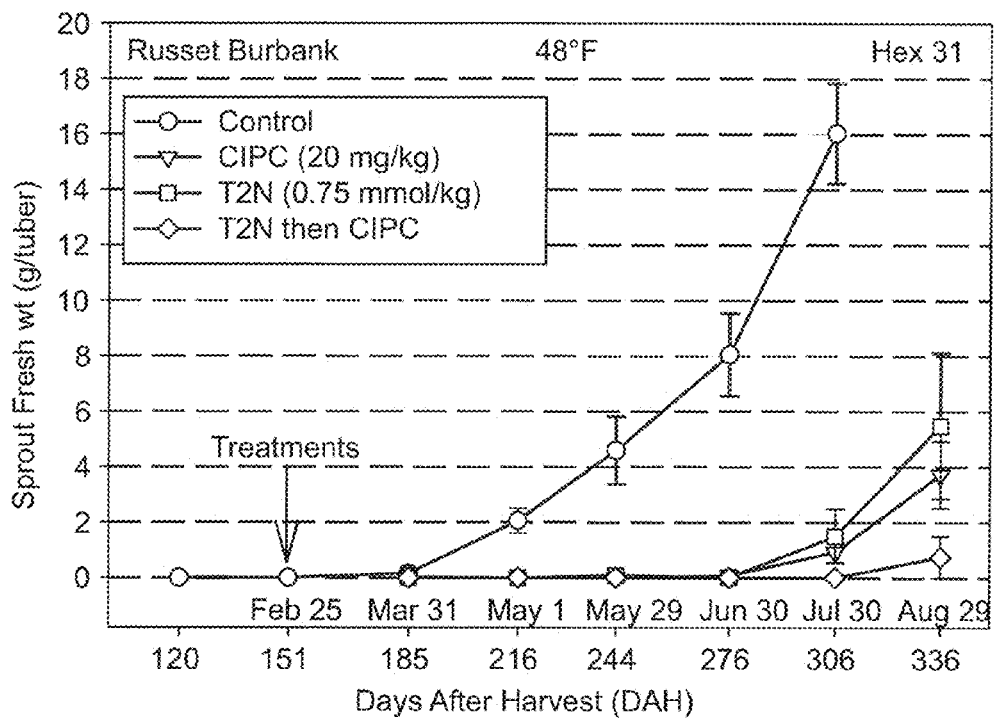
FIGS. 2A and B. Treatment with combination of T2N and CIPC. A, sprout growth in "Russet Burbank" tubers treated as indicated with CIPC, trans-2-nonenal, or trans-2-nonenal and CIPC in sequence; fresh weight of sprouts (g/tuber) at the indicated time points. CIPC, 20 mg/kg; T2N, 0.75 mmol/kg; B, photo of tubers.
Figure 2B:
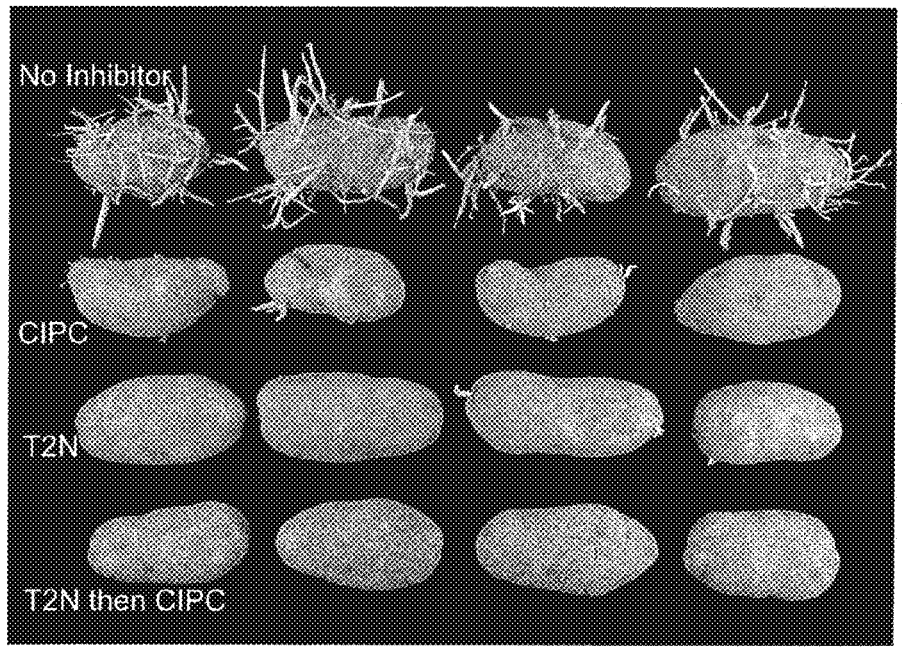

Following the emergence of Russet Burbank potato tubers from dormancy, CIPC and trans-2-nonenal were applied either alone or sequentially as indicated in FIG. 2A. All treatments were applied at 151 days after harvest (DAH). Sprout control was considered to end when one third of the tubers in the sample produced a sprout mass of greater than 50 mg/tuber or when the mean of the total sample exceeded 1 g/tuber. When both CIPC and trans-2-nonenal were used, the sprout-free interval of the tubers stored at 9° C. (48° F.) was significantly extended to 181 days compared to 124 days (CIPC alone) and 155 days (trans-2-nonenal alone) (FIGS. 2A and B). In this study, the application of CIPC was unconventional in that it occurred when tubers were beginning to sprout, as opposed to the window between wound healing and sprouting. CIPC provided additional sprout control on tubers whose actively growing sprouts were initially terminated by trans-2-nonenal, i.e. when used in combination with trans-2-nonenal. Trans-2-nonenal thus expands the window of opportunity for application of CIPC and this invention can therefore be useful to reduce the application rate and residues of CIPC.

Example 3

Use of α,β-Unsaturated and Aliphatic Carbonyl Compounds in Combination with CIPC to Enhance Sprout Inhibition of Potato tubers in Storage The objective of the experiment described below was to identify chemical sprout control regimes for season-long efficacy that will enable the use of significantly lower-than-label application rates of CIPC. The study used CIPC to extend the sprout-free period following an application of 3-decen-2-one or 2-decanone after sprouting occurs. Protocol.

This study, as described, used 3-decen-2-one (3D2). The study was duplicated as described with 2-decanone in place of 3D2. Tubers were stored at 9° C. until they emerged from dormancy (when 75% of the sample tubers are peeping, and the longest sprouts are no longer than 4 mm). At this time, 3-decen-2-one was applied at 0.75, 0.50, or 0.25 mmol/kg to 'burn off' growing sprouts. Each of these treatments was followed by applications of 1, 0.73, 0.47 or 0.20% a.i. of CIPC EC. The label rate of CIPC EC is 1% a.i. and results in a 10 mg/kg fresh wt application when applied as directed. Sprout measurements were obtained every two weeks. The length of the longest sprout on each tuber was recorded. The average length of the longest sprout was plotted over time for each treatment combination. The days to 10 mm were estimated from the second linear regression line of each element. Positive control treatments included the three rates of 3D2 alone and four post-sprouting concentrations of CIPC alone. The standard control treatment consisted of non-treated tubers.

TABLE 1

Days to average sprout length of 10 mm in 'Ranger Russet' treated with CIPC or 3-decen-2-one alone and in combination. Length of longest sprout was recorded every two weeks following application. There were 30 tubers per treatment.

| | mg kg$^{-1}$ fresh wt | | Days to 10 mm | |
|---|---|---|---|---|
| Trt | 3D2 | CIPC | Expected[1] | Actual |
| 1 | 116 | 10 | 152 | 140 |
| 2 | | 7.3 | 156 | 137 |
| 3 | | 4.7 | 137 | 113 |
| 4 | | 2.0 | 108 | 90 |
| 5 | | 0 | | 57 |
| 6 | 77 | 10 | 135 | 104 |
| 7 | | 7.3 | 139 | 119 |
| 8 | | 4.7 | 120 | 94 |
| 9 | | 2.0 | 91 | 72 |
| 10 | | 0 | | 40 |
| 11 | 39 | 10 | 133 | 110 |
| 12 | | 7.3 | 137 | 104 |
| 13 | | 4.7 | 118 | 97 |
| 14 | | 2.0 | 89 | 61 |
| 15 | | 0 | | 38 |
| 16 | 0 | 10 | | 95 |
| 17 | | 7.3 | | 99 |
| 18 | | 4.7 | | 80 |
| 19 | | 2.0 | | 51 |
| 20 | | 0 | | 22 |

[1]Theoretical days to 10 mm sprout length assuming an additive effect of CIPC and 3-decen-2-one. Values for single compound applications of the appropriate concentrations were added.
[2]Data are derived from the linear regression of the sprout growth curve for each treatment combination.

TABLE 2

Days to average sprout length of 10 mm in 'Ranger Russet' treated with CIPC or 2-decanone alone and in combination. Length of longest sprout was recorded every two weeks following application. There were 30 tubers per treatment.

| | mg kg$^{-1}$ fresh wt | | Days to 10 mm | |
|---|---|---|---|---|
| Trt | 2-decanone | CIPC | Expected[1] | Actual[2] |
| 1 | 116 | 10 | 161 | 171 |
| 2 | | 7.3 | 159 | 152 |
| 3 | | 4.7 | 162 | 108 |
| 4 | | 2.0 | 134 | 111 |
| 5 | | 0 | | 49 |
| 6 | 77 | 10 | 154 | 123 |
| 7 | | 7.3 | 152 | 162 |
| 8 | | 4.7 | 155 | 113 |
| 9 | | 2.0 | 127 | 92 |
| 10 | | 0 | | 42 |
| 11 | 39 | 10 | 146 | 122 |
| 12 | | 7.3 | 144 | 137 |
| 13 | | 4.7 | 147 | 112 |
| 14 | | 2.0 | 119 | 125 |
| 15 | | 0 | | 34 |
| 16 | 0 | 10 | | 112 |
| 17 | | 7.3 | | 110 |
| 18 | | 4.7 | | 113 |
| 19 | | 2.0 | | 85 |
| 20 | | 0 | | 25 |

[1]Theoretical days to 10 mm sprout length assuming an additive effect of CIPC and 2-decanone. Values for single compound applications of the appropriate concentrations were added.
[2]Data are derived from the linear regression of the sprout growth curve for each treatment combination.

Results:

The 116 mg kg$^{-1}$ rates of 3D2 and 2-decanone provided 58 and 50 days of control respectively following application with no subsequent treatment with CIPC (Tables 1 and 2). The 0.25 mmol/kg rate of 3D2 and 2-decanone provided approximately 1 month of control before sprouting re-occurred. CIPC alone, at the 1% a.i. rate (equivalent to 10 mg/kg fresh weight) exhibited 98 to 117 days sprout inhibition when applied post dormancy to tubers with actively growing sprouts. All combination treatments of 3D2 or 2-decanone followed immediately with CIPC treatment demonstrated a sprout control exceeding that of the 3D2 or 2-decanone and CIPC applied alone. In three instances, combinations of 2-decanone and CIPC exceeded the expected additive effect of the separate agents. These results demonstrate the efficacy of very low rates of CIPC when used in conjunction with various rates of 3D2 or 2-decanone to extend the sprout-free period in potato tubers.

REFERENCES

1. Gartrell, M. J., Craun, J. C., Podebarac, D. S., and Gunderson E. L. 1986. Pesticides, selected elements and other chemicals in adult total diet samples. October 1980-March 1982. J. Assoc. Off. Anal. Chem. 64:146-161.
2. Hartmans, K. J., Diepenhorst, P., Bakker, W., and Gorris, L. G. M. 1995. The use of carvone in agriculture—sprout suppression of potatoes and antifungal activity against potato tuber and other plant diseases. Industrial Crops and Products 4:3-13.
3 Knowles, N. R. and Knowles, L. O. 2005. Use of α,β-unsaturated aliphatic aldehydes and ketones to inhibit potato tuber sprouting. U.S. Pat. No. 6,855,669.
4. Lulai, E. C., Orr, P. H., and Glynn, M. T. 1997. Suppression of sprouting in stored potatoes using aromatic acids. U.S. Pat. No. 5,635,452.
5. Lulai, E. C., On, P. H., and Glynn, M. T. 1995. Natural suppression of sprouting in stored potatoes using jasmonates. U.S. Pat. No. 5,436,226.
6. Riggle, B. D. and Shafer, R. K. 1997. Sprout inhibition compositions comprising chlorpropham and substituted naphthalenes and methods of using same. U.S. Pat. No. 5,622,912.
7. Vaughn, S. F., Spencer, G. F., and Powell, R. G. 1992. Inhibition of potato sprouting using volatile monoterpenes. U.S. Pat. No. 5,139,562.
8. Vaughn, S. F., and Spencer, G. F. 1992. Aromatic aldehydes and alcohols as potato tuber sprout inhibitors. U.S. Pat. No. 5,129,951.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of inhibiting sprouting in potato tubers during storage, comprising
simultaneously or substantially simultaneously applying during storage of the potato tubers a composition comprising
i) one or more sprout inhibiting agents selected from the group consisting of
α,β-unsaturated aliphatic aldehydes;
α,β-unsaturated aliphatic ketones;
C3 to C14 saturated aliphatic aldehydes;
C3 to C14 saturated aliphatic ketones;
C3 to C14 saturated or unsaturated aliphatic primary alcohols;
C3 to C14 saturated or unsaturated aliphatic secondary alcohols; and
ii) one or more sprout inhibitors selected from the group consisting of chlorpropham (CIPC), dimethylnaphthalene (DMN), diisopropylnaphthalene (DIPN), carvone, and an essential oil.

2. The method of claim 1, wherein said one or more sprout inhibitors is CIPC and said CIPC is applied at a rate of 1-14 mg/kg of potato tubers.

3. The method of claim 1, wherein said method is carried out when sprouts begin to appear on said potato tubers.

4. The method of claim 1, wherein said essential oil is clove oil or mint oil.

5. The method of claim 1, wherein said one or more sprout inhibiting agents is trans-2-nonenal and said one or more sprout inhibitors is CIPC; or said one or more sprout inhibiting agents is 3-decen-2-one and said one or more sprout inhibitors is DMN; or said one or more sprout inhibiting agents 2-decanone and said one or more sprout inhibitors is DIPN; or said one or more sprout inhibiting agents is 3-decen-2-one and said one or more sprout inhibitors is clove oil; said one or more sprout inhibiting agents is 3-nonen-2-one and said one or more sprout inhibitors is CIPC.

6. A method of inhibiting sprouting in potato tubers during storage, comprising
applying one or more sprout inhibitors selected from the group consisting of chlorpropham (CIPC), dimethylnaphthalene (DMN), diisopropylnaphthalene (DIPN), carvone, and an essential oil to the potato tubers after wound healing and prior to sprouting at a rate that is lower than a label rate, and, when sprouts begin to appear,
applying during storage of the potato tubers one or more sprout inhibiting agents selected from the group consisting of
α,β-unsaturated aliphatic aldehydes;
α,β-unsaturated aliphatic ketones;
C3 to C14 saturated aliphatic aldehydes;
C3 to C14 saturated aliphatic ketones;
C3 to C14 saturated or unsaturated aliphatic primary alcohols; and
C3 to C14 saturated or unsaturated aliphatic secondary alcohols.

7. The method of claim 6, wherein the step of applying CIPC is carried out 2-8 weeks after transfer of the potato tubers to storage.

8. The method of claim 6, wherein the step of applying one or more sprout inhibiting agents is carried out 30-45 days after said step of applying CIPC.

9. The method of claim 6, further comprising the step of repeating the step of applying one or more sprout inhibiting agents multiple times during storage of the potato tubers.

10. The method of claim 9, wherein the step of repeating is performed at time intervals of from 4 to 12 weeks.

11. The method of claim 6, further comprising a step of applying maleic hydrazide (MH) to the potato tubers prior to harvest.

12. A composition for inhibiting sprouting of potato tubers during storage, comprising
i) one or more sprout inhibiting agents selected from the group consisting of
C8-C14 saturated or unsaturated aliphatic primary alcohols; and
C8-C14 saturated or unsaturated aliphatic secondary alcohols; and ii) one or more sprout inhibitors selected from the group consisting of chlorpropham (CIPC), dimethylnaphthalene (DMN), diisopropylnaphthalene (DIPN), carvone, and an essential oil.

13. The composition of claim 12, wherein said one or more sprout inhibitors is CIPC, and wherein said composition is formulated such that when applied, CIPC is applied at a rate of 1-14 mg/kg of potato tubers.

14. The composition of claim 13, further comprising one or more of dimethylnaphthalene (DMN), diisopropylnaphthalene (DIPN), carvone, and an essential oil.

15. The composition of claim 14, wherein said essential oil is clove oil or mint oil.

16. The composition of claim 12, wherein said composition comprises: trans-2-nonenal plus CIPC; 3-decen-2-one plus CIPC, or 3-nonen-2-one plus CIPC.

17. The method of claim 1, wherein said C3 to C14 alcohol is a primary or secondary C8 to C14 alcohol.

18. The method of claim 17, wherein said primary or secondary C8 to C14 alcohol is octanol.

19. The method of claim 6, wherein said C3 to C14 alcohol is a primary or secondary C8 to C14 alcohol.

20. The method of claim 19, wherein said primary or secondary C8 to C14 alcohol is octanol.

21. The composition of claim 12, wherein said C8-C14 saturated or unsaturated aliphatic primary alcohols is octanol.

22. The method of claim 6, wherein said one or more sprout inhibitors is CIPC and said lower-than-label rate is 1-14 mg/kg of potato tubers.

23. The method of claim 6, wherein said one or more sprout inhibitors is DMN and said lower-than-label rate is below 20 ppm.

24. The method of claim 6, wherein said one or more sprout inhibitors is DIPN and said lower-than-label rate is below 56 ppm.

* * * * *